United States Patent
Lewiner

(10) Patent No.: US 9,201,051 B2
(45) Date of Patent: Dec. 1, 2015

(54) METHOD AND DEVICE FOR DETECTING SMOKE

(75) Inventor: Jaques Lewiner, Saint-Cloud (FR)

(73) Assignee: FINSECUR, Nanterre (FR)

( * ) Notice: Subject to any disclaimer, the term of this patent is extended or adjusted under 35 U.S.C. 154(b) by 158 days.

(21) Appl. No.: 13/976,529

(22) PCT Filed: Dec. 28, 2011

(86) PCT No.: PCT/FR2011/053203
§ 371 (c)(1),
(2), (4) Date: Sep. 10, 2013

(87) PCT Pub. No.: WO2012/089986
PCT Pub. Date: Jul. 5, 2012

(65) Prior Publication Data
US 2013/0334417 A1    Dec. 19, 2013

(30) Foreign Application Priority Data

Dec. 31, 2010    (FR) ...................... 10 05201

(51) Int. Cl.
*G01N 21/53* (2006.01)
*G01N 33/00* (2006.01)
*G01N 15/06* (2006.01)
*G08B 17/107* (2006.01)

(52) U.S. Cl.
CPC ........ *G01N 33/0009* (2013.01); *G01N 15/0656* (2013.01); *G01N 21/53* (2013.01); *G08B 17/107* (2013.01)

(58) Field of Classification Search
CPC .............. G01N 21/53; G01N 33/0009; G01N 15/0656; G01N 27/624; G01N 27/68; G01B 17/11; G01B 17/107
USPC .......... 250/381, 389, 373, 384; 340/629, 630, 340/693.6, 693.5; 73/31.02
See application file for complete search history.

(56) References Cited

U.S. PATENT DOCUMENTS

| 3,823,372 A | 7/1974 | Hanson et al. |
| 3,932,851 A | 1/1976 | Rayl et al. |

(Continued)

FOREIGN PATENT DOCUMENTS

| EP | 0 236 223 A1 | 9/1987 |
| FR | 2 438 841 A1 | 5/1980 |
| FR | 2 594 953 A1 | 8/1987 |
| FR | 2 723 233 A1 | 2/1996 |
| FR | 2 746 184 A1 | 9/1997 |
| WO | 00/43965 A1 | 7/2000 |
| WO | 2007/051170 A2 | 5/2007 |

OTHER PUBLICATIONS

International Search Report, dated Mar. 15, 2012, from corresponding PCT application.

*Primary Examiner* — Yara B Green
(74) *Attorney, Agent, or Firm* — Young & Thompson

(57) ABSTRACT

The smoke detector includes: a chamber (1) provided with apertures (3) allowing the smoke to enter a detection area (D), a light source (S) configured to emit towards the detection area (D), and a light receiver (R) configured so as to receive the light coming from the detection area (D). A concentration element (6, 7) is provided so as to create a non-uniform electric field in the detection area (D), that, in the presence of smoke, can polarize smoke particles entering the detection area (D). The non-uniform electric field has a spatial gradient configured to exert a dielectrophoretic force on the smoke particles so as to drive the polarized smoke particles into a concentration zone (C) in the detection area (D) and to aggregate them together to form quasi "big particles".

20 Claims, 3 Drawing Sheets

(56) References Cited

U.S. PATENT DOCUMENTS

| | | | |
|---|---|---|---|
| 4,058,803 A * | 11/1977 | Scheidweiler | 340/629 |
| 4,225,860 A | 9/1980 | Conforti | |
| 4,469,953 A | 9/1984 | Fujisawa et al. | |
| 4,864,141 A | 9/1989 | Lewiner | |
| 5,351,034 A * | 9/1994 | Berger et al. | 340/577 |
| 5,477,218 A * | 12/1995 | Manmoto et al. | 340/630 |
| 5,864,293 A | 1/1999 | Lewiner et al. | |
| 2004/0163955 A1 | 8/2004 | Miles et al. | |
| 2006/0164241 A1* | 7/2006 | Makela et al. | 340/556 |
| 2013/0027211 A1* | 1/2013 | Mokhtari et al. | 340/629 |

* cited by examiner a   b c

FIGURE 3 :
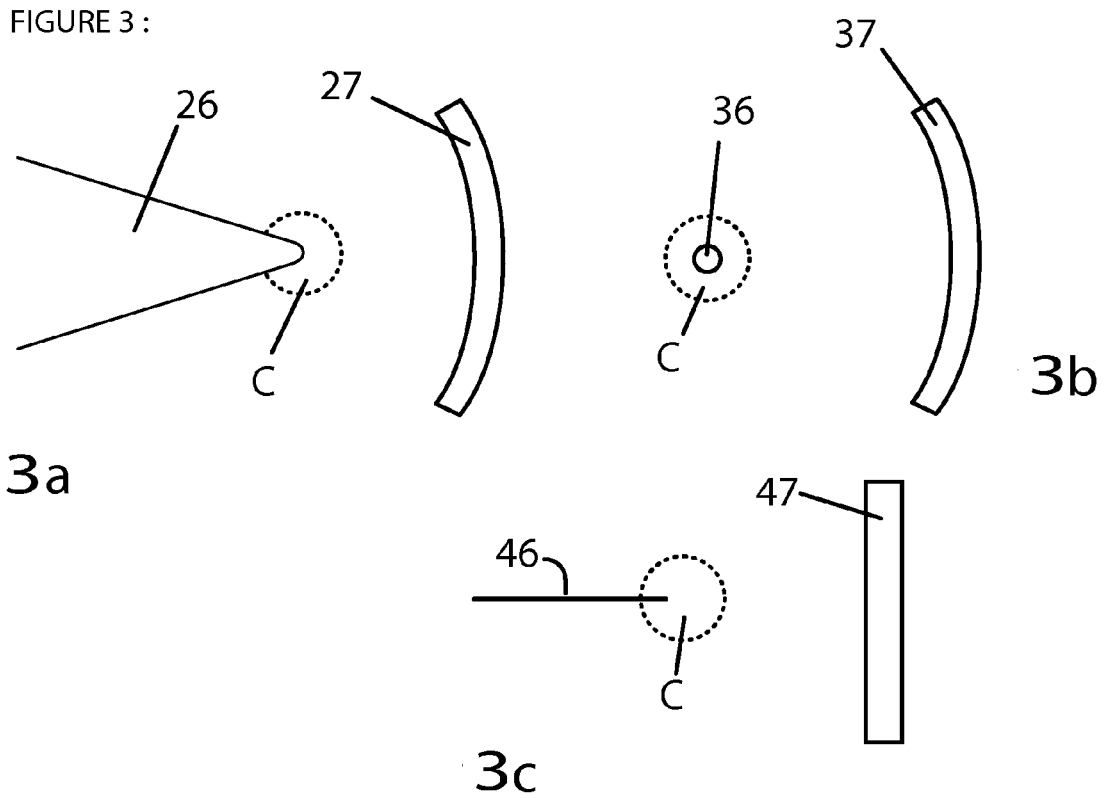
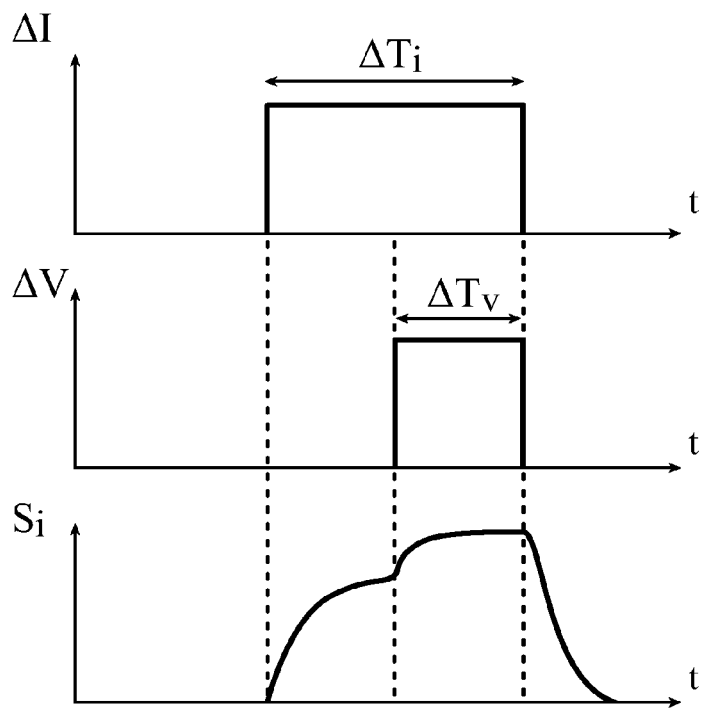
FIGURE 4 :

METHOD AND DEVICE FOR DETECTING SMOKE

BACKGROUND OF THE INVENTION

1. Field of the Invention

This invention relates to a device and a method for detecting smoke. It applies, in particular, to detecting a fire by means of the presence of fine particles or aerosols contained in the smoke, which makes it possible to reduce fire risks in premises where such devices are installed or where such methods are implemented.

2. Description of the Related Art

Two physical effects are mainly used to detect the presence of smoke, namely the diffusion of light by the smoke, dust or aerosols associated with it; and the change in the displacement speed of ions driven by an electric field as a result of this smoke, dust or aerosols.

In the first case, an optical smoke detector, as described for example in patent application FR 94 09473, comprises a chamber comprising apertures able to allow the smoke to enter into the chamber, a light source that can, when powered, emit a light beam into the chamber, a light receiver able to transform the reception of light into an electric reception signal, the interior of the chamber being weakly reflective in the spectral range of the light emitted by the source, the apertures being associated to chicanes able to prevent exterior light penetrating directly into the chamber and the source and the receiver being placed so as to able to prevent the light emitted by the source reaching the receiver directly.

Thus, in the absence of smoke containing particles large enough to diffuse the light emitted by the source, typically greater than 100 nm in size, the receiver receives practically no light and thus provides only a very weak electric reception signal, due solely to the light that penetrates from outside the chamber and to several possible reflections on the chamber's inner walls from the light emitted by the source.

In contrast, the presence of smoke or aerosols, associated with particles larger than 100 nm in the light beam, results in the appearance of diffused beams, some of which reach the receiver, possibly after being reflected on the chamber's inner walls, producing an electric reception signal.

Thus, this signal exceeding a predefined threshold allows an alarm to be triggered or sent.

Optical smoke detectors are especially sensitive to visible smoke, i.e. comprising large particles, but remain relatively insensitive to smoke comprised of fine particles, and thus almost invisible, which is emitted during the fire's first stages of development or in a hot fire.

In effect, when the smoke consists of fine particles that are too small or in too low a concentration, there is a very low level of light diffusion and the receiver receives an insufficient amount of light to allow the threshold for triggering or sending an alarm to be exceeded.

In the second case, an ionic smoke detector comprises a chamber in which two measurement electrodes are arranged between which qi charged ions are created or brought.

Applying a potential difference between these electrodes produces an electric field E which exerts a force $F=q_i \times E$ on these ions; this produces a nominal electric current between the electrodes and in the external circuit that connects them, this electric current depending in particular on the amount of ions present in the chamber, the potential difference applied between the measurement electrodes, and the mobility of the ions.

Means of measuring this current are also provided, which provide a signal that can be used by processing means.

When particles associated with smoke enter the chamber, some of these particles become attached to the chamber's ions as a result of the electrostatic forces created by these ions; this reduces their mobility and has the effect of reducing the electric current.

If the voltage applied to the electrodes is low enough, typically between 5 and 30 volts, the nominal electric current is also low, typically between 10 µA and 100 µA, and the slowing down of the ions resulting from the presence of the particles is such as to reduce the amplitude of this current very substantially.

The processing means are arranged so as to allow an alarm to be triggered or sent when the current measured is below a predefined threshold.

Air ionization devices are more sensitive to combustion products, emitted during the initial development of fires or in hot fires; the size of these products can reach values of several tens of nm, or less, and thus allow alarms to be triggered earlier than optical devices, thus making it possible to limit the consequences of these fires.

Two approaches have been used to create ions in the measuring chamber: either by ionizing the air using a small radioactive source, as described, for example, in patent application FR 86 02567, or by creating an electric field stronger than the electric field for air breakdown, as described, for example, in patent U.S. Pat. No. 3,823,372.

The first approach is simple to implement and not very costly.

For example, a source of α particles comprised of Am-241 with activity between 0.1 and 1 microcurie is used; these particles can cross a distance of the order of centimeters in the air and thus ionize the volume passed through.

However, although this solution makes it possible to detect fires early and thus reduce their consequences, it is facing increasing challenges, either from users themselves, who are reluctant to increase radioactive sources in their premises, or from manufacturers' sales departments, who are confronted by negative reactions from their customers, or from regulations.

With regards to the second approach, various solutions have been proposed for ionizing the air. These approaches use the fact that, by applying a potential difference above a certain threshold Vs between two electrodes, one can initiate a process of electrical discharge and thus create ions.

The value Vs depends on several parameters, such as the nature of the gas between the electrodes, the pressure of the gas separating them, the distance between the electrodes and their shape, the presence of dust or humidity, etc.

In the air, this threshold is considered to be approximately 330 V for distances between electrodes of the order of micrometers, distances too small to be used directly in a smoke detector, which means that voltages of several kilovolts must be used to create this ionization.

However, values such as these cannot be used for polarizing the measurement electrodes since the high speed of the ions resulting from this would lead to a very high nominal electric current and these ions would cross the measurement chamber in a very short period of time.

As a result, the changes in this current because of the presence of particles associated with smoke would be so small that they would be difficult to detect.

To overcome this obstacle, various proposals have been made to increase the interaction time between the ions and the smoke particles.

A first approach has been to use a measurement chamber polarized by a weak voltage, into which ions produced in an ionization chamber polarized by a high voltage are transferred, by means of a weak current of air, and thus to have a low nominal current.

An example of such a solution is described in patent application FR 96 03296.

In a second approach, reflective elements have been introduced between the electrodes of an ionization chamber polarized by a high voltage, so as to increase the interaction time.

An example of such a solution is described in patent application U.S. Pat. No. 3,932,851.

These alternative solutions utilize high electric voltages which, however, result either in detectors that have relatively low detection sensitivities due to the very fact of using high voltages, reducing their advantages, or in devices that are mechanically complex, fragile and expensive.

In addition, the response of these detectors is also influenced by parameters such as variations in ambient gas pressure or in temperature, thus requiring compensation devices such as, for example, described in patent EP-236 223, to be used as well.

For these reasons there have been no major industrial developments of these alternative solutions.

In order to allow both small- and large-sized particles to be detected, and thus to cover the risks associated with the various phases of a fire, combining ionic smoke detection devices, well suited to detecting small particles, and optical smoke detection devices, well suited to detecting larger particles, inside the same detector, has been proposed, for example in patent U.S. Pat. No. 4,469,953.

In this case, so as to allow chambers to be constructed that are electromagnetically shielded and optically weakly reflective, and also not very expensive, it has been proposed, as described, for example, in patents U.S. Pat. Nos. 4,469,953 and 4,225,860, to produce the electrodes or shields using conductive plastics rather than using metal parts.

Clearly, the ionic portion of these detectors has the same drawbacks as detectors that operate solely in ionic mode, as described above.

BRIEF SUMMARY OF THE INVENTION

This invention aims to remedy all or part of these drawbacks.

To this end, according to a first aspect, this invention envisages a smoke detector.

According to a second aspect, this invention envisages a method for detecting smoke according to the independent method claim.

Thus, as a result of the field created by the concentration means, a neutral smoke particle with polarizability $\alpha$ acquires an electric dipole moment and is subjected to a force proportional to the product of $\alpha$ and the square of the electric field gradient, which results in it being attracted towards the high-gradient concentration area, thus producing a concentration of particles to be detected in this concentration area.

In addition, in the region where smoke particles are concentrated, because of the polarization they have acquired, the particles tend to aggregate and thus form "quasi" large particles configured to provide good diffusion of the light received from the light source, even if the smoke particles forming the aggregate are not large enough, or in a sufficient concentration, to diffuse the light by themselves.

The concentration means can comprise electrodes configured to create a non-uniform electric field in at least one portion of the detection area, and/or a focusing device configured to focus light rays in the detection area, to generate electromagnetic field gradients in the detection area.

In preferred embodiments one and/or the other of the following layouts are used:

- the non-uniform electromagnetic field is configured to aggregate the smoke particles in the concentration area so as to form larger smoke particles;
- the spatial electric field gradient is configured to exert a dielectrophoretic force on the smoke particles between 0.01 µm and 10 µm in size;
- the concentration means comprise two electrodes configured to create a non-uniform electric field in at least one portion of the detection area, the electrodes being configured so as to create a spatial electric field gradient in the detection area when a potential difference below the ionization threshold of the gas in the chamber is applied to these electrodes;
- a portion of the chamber itself constitutes one of the electrodes;
- when a portion of the chamber itself constitutes one of the electrodes, the chamber is formed from a conductive polymer;
- when a portion of the chamber itself constitutes one of the electrodes, one of the electrodes comprises irregularities with a small radius of curvature;
- means are configured to apply voltage pulses with amplitude $\Delta V$ and duration $\Delta Tv$ to the electrodes;
- the amplitude of the voltage pulses is between 2 and 300 V;
- the amplitude of the voltage pulses is between 2 and 30 V;
- the electrodes are made of or covered in a material configured to reduce or prevent the adherence of dust on their outer surface and/or humidity on the high electric field gradient sub-area;
- the electrodes are covered by a hydrophobic layer;
- the electrodes are covered by a hydrophobic layer containing a fluorinated polymer;
- the concentration means comprise a focusing device configured to focus light rays in the detection area, to generate electromagnetic field gradients in the detection area. The light rays to be focused can be emitted by the light source or by a second light source separate from the light source;
- the focusing device is configured to focus light rays in the infrared spectrum;
- the focusing device comprises a lens, a prism or a light guide;
- the means powering the source supply current pulses with amplitude $\Delta I$ and duration $\Delta Ti$;
- the duration of the current pulses is between 100 ns and 10 ms;
- the current pulses are emitted at time intervals of between 100 ms and 10 s;
- the processing means are configured to analyze the temporal variation in the electric signal's amplitude;
- the processing means are configured to compare the signal's amplitude to a reference level;
- the reference level is fixed;
- the reference level is determined by means;
- the means are configured to modify the reference level according to values of the electric signal measured previously;
- the means are configured to modify the reference level according to values of the mean electric signal measured previously;
- the means are configured to modify the reference level according to the nature of the fire risk to be monitored;
- when a portion of the chamber itself constitutes one of the electrodes, the other electrode is located between the emitter and the receiver and prevents the receiver from having a direct view of the emitter;

in the above case, said other electrode has a sharp edge in a direction perpendicular to the emitter/receiver direction;

one of the electrodes is a conductive wire placed parallel to the propagation axis of the light emitted by the source;

in the above case, the radius of the wire is between 10 μm and 1 mm;

the radius of the wire is between 20 μm and 200 μm;

one of the electrodes is formed by the edge of a prism, this edge being placed parallel to the propagation axis of the light emitted by the source;

the radius of curvature of the above edge is between 10 μm and 1 mm;

the above radius is between 20 μm and 200 μm;

in one of the above six cases, the propagation axis of the light is positioned between the area of high curvature of the wire or of the edge and the second electrode;

in the above case, the distance between the electrodes configured to create a non-uniform electric field in at least one portion of the detection area is between 2 and 10 mm.

the light source is a diode laser;

the axis of maximum sensitivity of the light receiver and its associated optical system and the axis of maximum emission of the light source and its associated system are configured such that the light rays coming from the detection area form an angle of between 120 and 140 degrees with the light rays arriving in the detection area from the light source and its associated system;

the windows are covered by grilles filtering particles greater than 1 mm in size;

the size of the holes forming the windows is between 50 μm and 500 μm;

the size of the holes forming the windows is between 100 μm and 400 μm;

the windows are comprised of sheets with apertures and are covered, at least on their portion outside the chamber, in a hydrophobic material;

the voltage pulses ΔV and current pulses ΔI are applied simultaneously;

the voltage pulses ΔV are applied with a delay ΔT1 after the current pulses ΔI are emitted;

the delay ΔT1 is between 1 and 60 μs;

the delay ΔT1 is between 10 and 30 μs;

the duration ΔTi of the current pulse ΔI is between 20 and 60 μs, the duration ΔTv of the voltage pulse ΔV is between 20 and 60 μs and the delay ΔT1 is between 20 and 60 μs;

the duration ΔTi of the current pulse ΔI is 50 μs, the duration ΔTv of the voltage pulse ΔV is 25 μs and the delay ΔT1 is 25 μs;

the voltage pulses ΔV are emitted with a delay ΔT2 after the current pulses ΔI are applied;

the delay ΔT2 is between 1 and 60 μs;

the delay ΔT1 is between 10 and 30 μs;

the duration ΔTi of the current pulse ΔI is between 20 and 60 μs, the duration ΔTv of the voltage pulse ΔV is between 20 and 60 μs and the delay ΔT2 is between 20 and 60 μs, the duration ΔTi of the current pulse ΔI is 50 μs, the duration ΔTv of the voltage pulse ΔV is 25 μs and the delay ΔT2 is 25 μs;

the voltage pulses ΔV are only emitted with certain current pulses ΔI, the light source is a light-emitting diode;

the light source is a diode laser; and the wavelength of the light emitted by the source is between 800 nm and 1000 nm.

Thus, according to these embodiments of the invention, one has a simple, inexpensive device that makes it possible to detect smoke with large particles, such as an optical detector would, and smoke with fine particles or aerosols, such as an ionic detector would, without using radioactive sources or high electric voltages.

Other than these main provisions, the invention comprises certain other provisions that are preferably used at the same time and which will be described below.

BRIEF DESCRIPTION OF THE DRAWINGS

In what follows, some preferred embodiments of the invention will be described with reference to the appended figures in a clearly non-limiting way.

FIG. 3 is a graphic representation in a top view of three examples of electrode geometry according to particular embodiments, configured to create an electric field gradient when a potential difference is applied between these electrodes:

FIG. 3a: tip/cylinder,

FIG. 3b: wire/cylinder,

FIG. 3c: edge/plane.

FIG. 4 is an example of temporal representation of the changes in the reception signal Si when a current pulse ΔI is applied to a light source and a voltage pulse ΔV is applied between the electrodes according to particular embodiments.

DETAILED DESCRIPTION OF THE PREFERRED EMBODIMENTS

Figure 1:
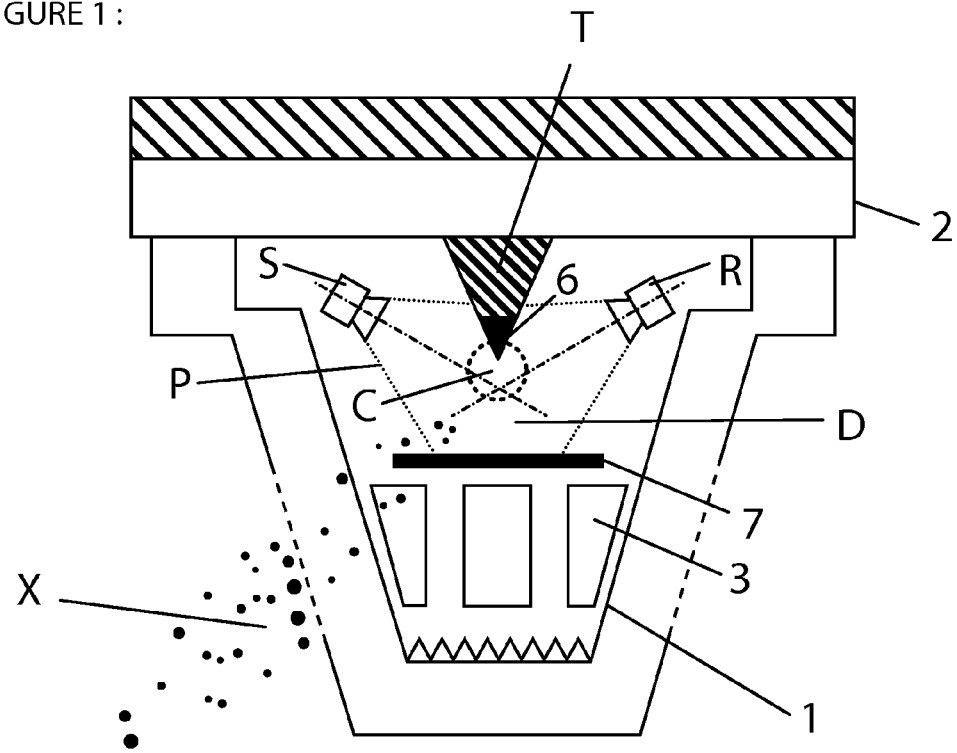
FIG. 1 represents, schematically, a first particular embodiment of the smoke detector device that is the subject of the invention.

A smoke detector according to a first embodiment of the invention is represented schematically in FIG. 1. This smoke detector comprises a chamber 1, pierced, in a manner know per se, by apertures 3 to allow the air and smoke particles to be inspected to pass towards a detection area D inside the chamber 1.

These apertures 3 are associated to chicanes, making it possible to limit the penetration of outside light into the chamber. The internal walls of the chamber 1 are configured to reflect the light rays as little as possible.

The apertures 3 can be covered by grilles filtering particles greater than 1 mm in size. In this embodiment of the invention, the size of the holes forming the apertures is between 50 μm and 500 μm, and preferably between 100 μm and 400 μm The apertures 3 can be comprised of sheets with apertures and are covered, at least on their portion outside the chamber, in a hydrophobic material.

The chamber contains at least one light source S, for example a diode laser or a light-emitting diode, configured to emit a beam of light rays P towards the detection area D when it receives an electric current supplied by electrical power supply means; and at least one light receiver R sensitive to at least one portion of the wavelengths of the light rays emitted by the light source S and configured to transform the reception of light into an electric reception signal.

The receiver R is placed in a shadow area of the chamber 1 with regard to the light source S to prevent the light emitted by the light source S reaching the receiver R directly.

In this embodiment, this shadow area is created by means of a small separator part or optical wall T placed between the light source S and the receiver R to prevent the light emitted by the light source S directly reaching the receiver R. Thus, the light source S is positioned on one of the sides of the wall T and the receiver R is placed on the other side of the wall T so that light rays cannot circulate directly from the light source S to the receiver R. The optical wall T has two opposite surfaces that are crenellated to reflect the light rays as little as possible.

The receiver R is configured to receive, in the presence of smoke particles or aggregates of smoke particles in the detection area D, diffused light coming from the detection area D.

If no smoke is present in the detection area D of the chamber when the beam of light rays P is emitted, the receiver R receives only the narrow beams of light possibly reflected by the inner walls of the chamber 1, with the result that the electric signal supplied by the receiver is very weak, even practically zero.

In contrast, if the chamber 1 contains smoke in the detection area D, the associated particles X are likely to cause the light to be diffused such that the receiver R can receive some of the rays thus diffused, which produces an electric signal on output from the detector R.

This signal is sent to processing means configured to compare the signal's amplitude to a reference level and to analyze its temporal dependence.

This signal exceeding a certain threshold or the change in its temporal dependence, also above a defined limit, allows an alarm to be triggered or sent.

The higher the density of the smoke in question and the larger the associated particles, the greater the amplitude of this signal is.

The inventor has noted that, by using special properties of the matter and its behavior in certain electric fields with a very specific geometry, it was possible to concentrate the smoke particles in certain regions of the chamber 1, referred to as concentration region C, and to create aggregates of fine particles configured to diffuse the light emitted by the light source S even if the fine smoke particles making up the aggregates did not have a directly detectable effect on this light.

To achieve this, concentration means (6, 7, 16, 17, 26, 27, 36, 37, 46 and 47 in the figures) are placed inside the chamber 1, which are configured to create at least one sub-area within the chamber 1 in the detection area D, referred to as "high-gradient sub-area", wherein a high electric or electromagnetic field gradient is created. In effect, these concentration means are configured so as to create a non-uniform electric field in the detection area D of the chamber 1, which is configured to polarize smoke particles entering the detection area D in the presence of smoke, the non-uniform electric field having a spatial electric field gradient configured to exert a dielectrophoretic force on the smoke particles present in the non-uniform electric field, this dielectrophoretic force being configured to drive the polarized smoke particles into a concentration sub-area C, which corresponds to the so-called high-gradient sub-area in the detection area D and towards each other, resulting in the formation of aggregates.

According to the first embodiment of the invention shown in FIG. 1, these concentration means are comprised of two electrodes, 6 and 7, positioned in the chamber in the detection area D and configured so as to create an electric field having a high field gradient in a concentration region C of the detection area D when a voltage V is applied between these electrodes 6 and 7.

Applying the voltage V between the electrodes 6 and 7 creates a field gradient configured to generate a dielectrophoretic effect, in the concentration region C, on the fine smoke particles, e.g. between 0.01 µm and 10 µm in size. It is noted that dielectrophoresis is an effect that creates a force on a dielectric particle when it is subjected to a high-gradient non-uniform electric field. Thus, as a result of the electric field, a neutral smoke particle with polarizability α acquires an electric dipole moment and is subjected to a force proportional to the product of α and the square of the electric field gradient, which, irrespective of the polarity of the voltage applied, results in it being attracted towards the high-gradient area, thus producing a concentration of particles to be detected in this high-gradient area, referred to as concentration region C.

In addition, in the concentration region C of the smoke particles, because of the polarization they have acquired as a result of the electric field, these particles tend to aggregate and thus form "quasi" large particles configured to provide a high level of diffusion of the light received from the light source S, in the detection area D, even if the particles forming the aggregate are not large enough, or not in a sufficient concentration, to diffuse the light.

Figure 2:
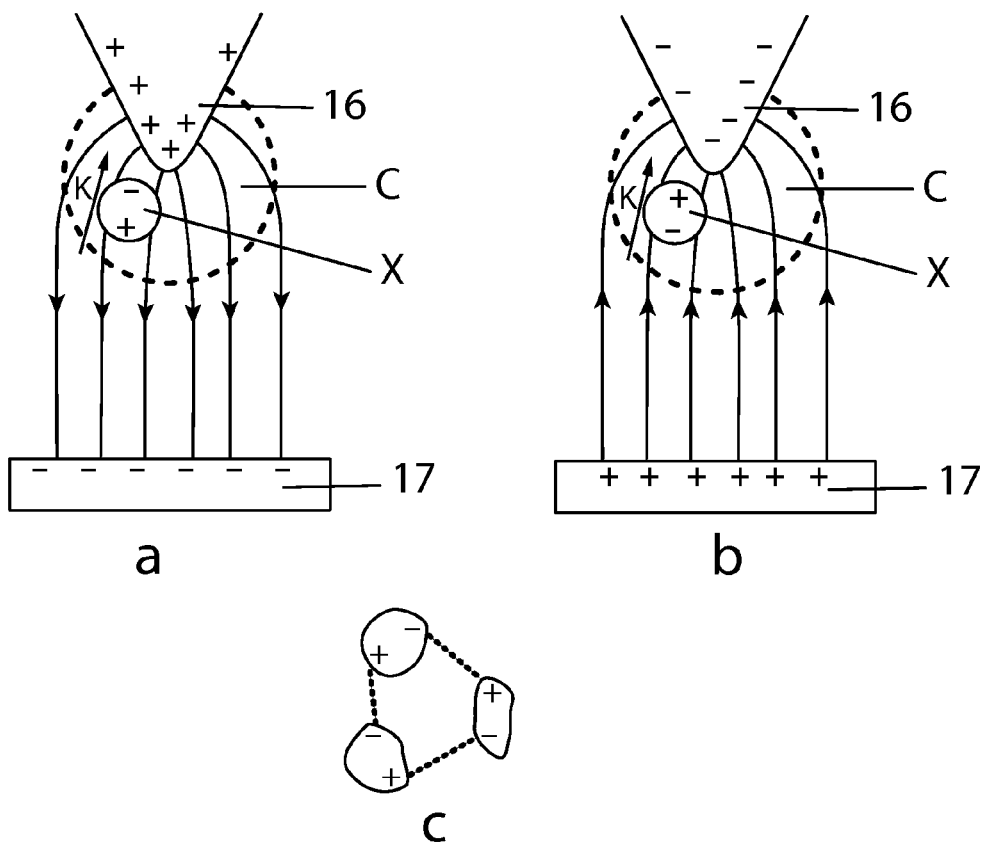
FIGS. 2a and 2b describe, schematically, the pattern of the electric field lines between two electrodes of shapes configured to create an area of high field gradient according to particular embodiments, between which smoke particles are located, these particles, although neutral, being subjected to a force in the direction K.
FIG. 2c describes, schematically, the attraction effect between the different particles as a result of their induced polarization.

FIGS. 2a and 2b show, schematically, the pattern of the electric field lines between two electrodes 16 and 17 which, when a voltage V is applied between the two electrodes, create an area of high field gradient, between which smoke particles are located that are subjected to a force in the direction K.

FIG. 2c shows, schematically, the attraction effect between the different smoke particles as a result of their induced polarization.

Many geometric configurations of the electrodes are possible in order to obtain high electric field gradients: in the example represented in FIG. 1, a voltage is applied between a tip 6, for example metallic, and a flat conductive surface 7, for example made of a conductive plastic.

It is also possible to obtain electric field gradients that generate the dielectrophoretic effect by using in the same way a conductive tip 16 and a conductive surface 17, as represented in FIG. 2a or 2b, or, as represented in FIG. 3a, a conductive tip 26 and a cylindrical surface 27 or, as represented in FIG. 3b, a cylindrical conductive segment of wire 36 and a portion of an arc 37 of a cylindrical conductive surface or, as represented in FIG. 3c, the edge of a conductive plane 46 and a conductive plane 47 or according to any other method otherwise known.

If charged smoke particles are also present, they are directly driven by the electric force F, with F being equal to the product of q, the particle's electrical charge, and E, the electric field generated by the application of the voltage between the electrodes (6, 7, 16, 17, 26, 27, 36, 37, 46 and 47).

In this way, it is possible to concentrate the smoke particles in a predefined concentration region C of the detector such that the light ray coming from the light source S and incident in this concentration region C is diffused towards the receiver R by this high concentration of smoke particles, which results in increasing the detector's sensitivity.

In embodiments of the invention, a portion of the chamber itself constitutes one of the electrodes. When a portion of the chamber itself constitutes one of the electrodes, the chamber can be formed from a conductive polymer. When a portion of the chamber itself constitutes one of the electrodes, one of the electrodes can comprise irregularities with a small radius of curvature. When a portion of the chamber itself constitutes one of the electrodes 7, the other electrode is located between the emitter and the receiver to prevent the receiver from having a direct view of the emitter. Said other electrode can have a sharp edge in a direction perpendicular to the emitter/receiver direction.

In embodiments, one of the electrodes comprises a conductive wire placed parallel to the propagation axis of the light emitted by the light source. The radius of the wire can be between 15 µm and 1 mm, and preferably between 20 µm and 400 µm.

In embodiments, one of the electrodes is formed by the edge of a prism, this edge being placed parallel to the propagation axis of the light emitted by the source. The radius of curvature of the above edge can be between 15 µm and 1 mm, and preferably between 100 µm and 500 µm. The propagation axis of the light from the light source S is positioned between the area of high curvature of the wire or of the edge and the second electrode.

The power supply means can be configured to apply voltage pulses with amplitude $\Delta V$ and duration $\Delta Tv$ to the electrodes (6, 7, 16, 17, 26, 27, 36, 37, 46 and 47). The amplitude of the voltage pulses can be between 2 and 300 Volts, and preferably between 2 and 30 Volts.

In embodiments of the invention, the electrodes can be made of or covered in a material configured to reduce or prevent the adherence of dust on their outer surface and/or humidity on the high electric field gradient concentration sub-area C. The electrodes can be covered by a hydrophobic layer, and preferably by a hydrophobic layer containing a fluorinated polymer.

The power supply means of the light source S can be configured to supply the light source S with current pulses with amplitude $\Delta I$ and duration $\Delta Ti$. The duration of the current pulses can be between 100 ns and 1 ms. The current pulses can be emitted at time intervals of between 100 ms and 10 s.

The voltage pulses supplied to the electrodes and the current pulses supplied to the light source S can be applied simultaneously, or the voltage pulses can be applied with a delay $\Delta T1$ after the current pulses are emitted. The delay $\Delta T1$ can be between 1 µs and 60 µs, and preferably between 10 and 30 µs.

The duration $\Delta Ti$ of the current pulse $\Delta I$ can be between 20 and 60 µs, the duration $\Delta Tv$ of the voltage pulse $\Delta V$ can be between 20 and 60 µs and the delay $\Delta T1$ can be between 20 and 60 µs.

The duration $\Delta Ti$ of the current pulse $\Delta I$ can be 50 µs, the duration $\Delta Tv$ of the voltage pulse $\Delta V$ can be 25 µs and the delay $\Delta T1$ can be 25 µs.

The voltage pulses $\Delta V$ can be emitted with a delay $\Delta T2$ after the current pulses $\Delta I$ are applied. The delay $\Delta T2$ can be between 1 and 60 µs, and preferably between 10 and 30 µs.

The duration $\Delta Ti$ of the current pulse $\Delta I$ can be between 20 and 60 µs, the duration $\Delta Tv$ of the voltage pulse $\Delta V$ can be between 20 and 60 µs and the delay $\Delta T2$ can be between 20 and 60 µs.

The duration $\Delta Ti$ of the current pulse $\Delta I$ can be 50 µs, the duration $\Delta Tv$ of the voltage pulse $\Delta V$ can be 25 µs and the delay $\Delta T2$ can be 25 µs.

In embodiments of the invention, the voltage pulses are only emitted with certain current pulses.

The means of processing the reception signal can be configured to analyze the temporal variation in the amplitude of the electric reception signal of the receiver R.

These processing means can be designed to compare the signal's amplitude to a reference level. The reference level can be fixed and determined by reference means. The reference means can be configured to modify the reference level according to values of the electric signal measured previously, or according to values of the mean electric signal measured previously. The reference means can be configured to modify the reference level according to the nature of the fire risk to be monitored.

FIG. 4 is an example of temporal representation of the changes in the reception signal Si when a current pulse $\Delta I$ is applied to the light source and a voltage pulse $\Delta V$ is applied between the electrodes.

It goes without saying, and as is demonstrated moreover in the preceding description, that the invention is in no way restricted to those modes of application and embodiments that have been more particularly envisaged. On the contrary, it encompasses all variants of it, in particular those in which the narrow beam of light P coming from a light source, such as an emitting diode laser S, is propagated along the high gradient area created near the electrode since the probability of the smoke particles X interacting with the light beam P is thus significantly increased.

In variants, the electromagnetic field gradients are created by focusing light rays, for example in the infrared spectrum, in very localized areas inside the chamber, using focusing systems known per se, such as lenses, prisms or light guides.

Figure 5:
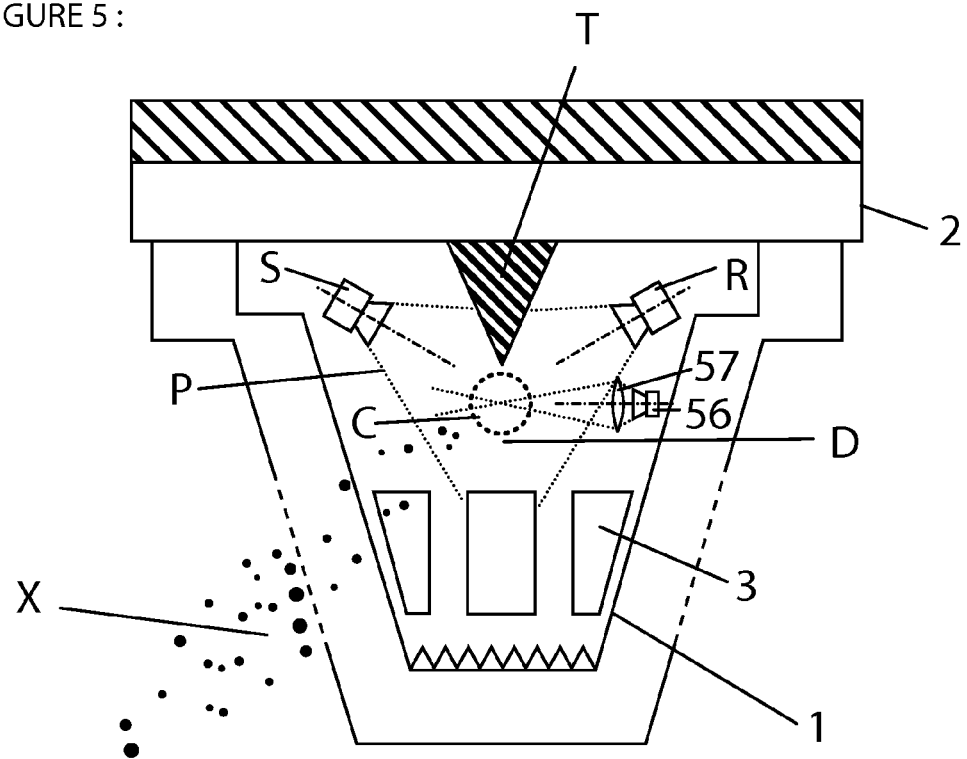
FIG. 5 represents, schematically, a smoke detector according to a second particular embodiment of the device that is the subject of the invention.

Thus, according to a second embodiment of the invention shown in FIG. 5, the concentration means are comprised of a source of light rays 56 in the infrared spectrum, e.g. a diode laser or a light-emitting diode, and a lens 57 configured to focus the light rays in the detection area D, so as to create a concentration area C. This area corresponds to the so-called high-gradient sub-area.

In this way, it is possible to concentrate the smoke particles in the predefined concentration region C of the detector such that the light ray coming from the light source S and incident in this concentration region C is diffused towards the receiver R by this high concentration of smoke particles, which results in increasing the detector's sensitivity.

Of course, in variants the light source S itself is used to supply these light rays for creating the concentration area C.

Figure 6:
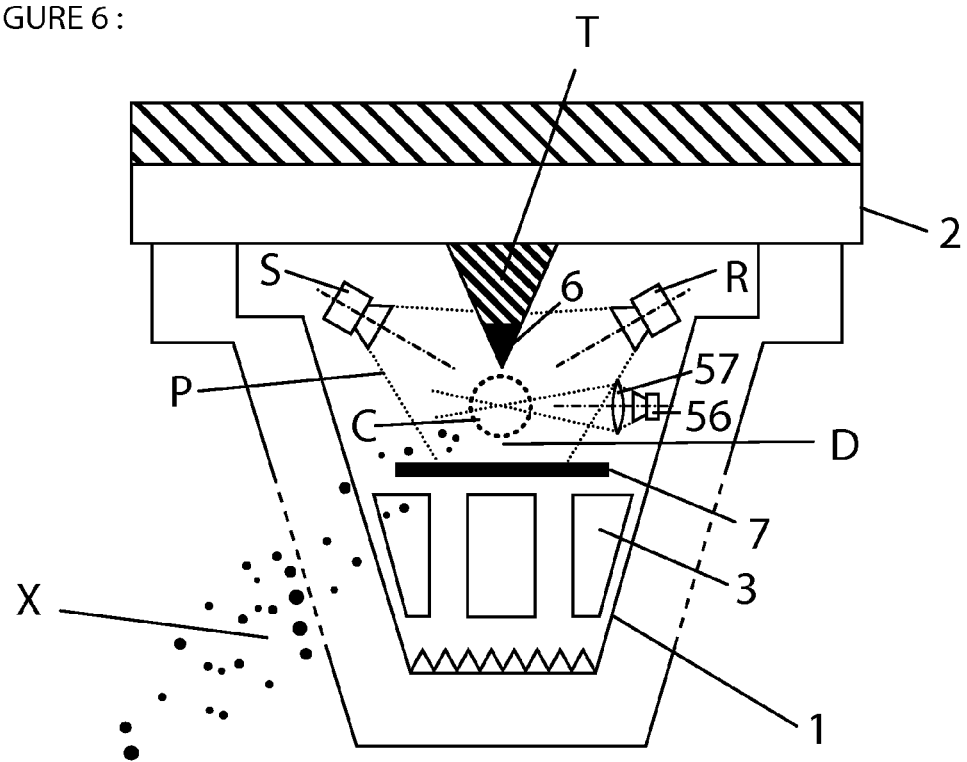
FIG. 6 represents, schematically, a smoke detector according to a third particular embodiment of the device that is the subject of the invention.

In other variants, such as the one illustrated in the third embodiment of the device that is the subject of the invention in FIG. 6, the concentration means comprise electrodes 6 and 7 for creating a concentration region, and a source of light rays 56 in the infrared spectrum and a lens 57 for improving the concentration of smoke particles in the concentration region C.

Here again, and as is demonstrated moreover in the preceding description, this third embodiment is in no way restricted to those modes of application and embodiments that have been more particularly envisaged. On the contrary, this embodiment encompasses all variants of it, in particular those where the narrow beam of light P is itself used to create the high-gradient areas utilizing the focusing means described above.

Consequently, and irrespective of the embodiment adopted, the result is an optical detection device whose composition and operation are adequately reflected in the preceding description.

Compared to currently known devices, this device has many advantages, in particular much greater sensitivity to fine smoke or weak concentrations of smoke.

The invention claimed is:

1. A smoke detector, comprising:
   a chamber provided with apertures configured to allow the smoke to enter a detection area in the chamber;
   a light source configured to emit a beam of light rays towards the detection area;
   a light receiver sensitive to at least one portion of the wavelengths of the light rays emitted by the light source and configured to transform the reception of light into an electric reception signal;
   concentration means configured to create a non-uniform electromagnetic field in at least one portion of the detection area, that, in the presence of smoke, can polarize smoke particles entering the detection area, the non-uniform electromagnetic field having a spatial electromagnetic field gradient configured to exert a dielectrophoretic force on the smoke particles configured to drive the polarized smoke particles into a concentration area in the detection area.

2. The smoke detector according to claim 1, wherein the spatial electric field gradient is configured to exert a dielectrophoretic force on the smoke particles between 0.01 µm and 10 µm in size.

3. The smoke detector according to claim 1, wherein the concentration means comprise two electrodes configured to create a non-uniform electric field in at least one portion of the detection area, the electrodes being configured to create a spatial electric field gradient in the detection area when a potential difference V, below a ionization threshold of the gas in the chamber, is applied to these electrodes.

4. The smoke detector according to claim 3, wherein a portion of the chamber itself constitutes one of the electrodes, the chamber being formed from a conductive polymer.

5. The smoke detector according to claim 3, further comprising means of applying the voltage V to the terminals of the electrodes, configured to apply voltage pulses with amplitude ΔV between 2 and 300V and duration ΔTv to the electrodes.

6. The smoke detector according to claim 3, wherein one of the electrodes is formed from a conductive tip, a segment of a cylindrical conductive wire or a conductive edge and the other electrode is formed from a flat conductive surface or a portion of an arc of a cylindrical surface.

7. The smoke detector according to claim 3, wherein a portion of the chamber itself constitutes one of the electrodes, and the other electrode is located between the light source and the receiver and prevents the receiver from having a direct view of the light source.

8. The smoke detector according to claim 3, wherein one of the electrodes is a conductive wire placed parallel to a propagation axis of the light emitted by the light source.

9. The smoke detector according to claim 8, wherein the radius of the conductive wire is between 10 µm and 1 mm.

10. The smoke detector according to claim 3, wherein one of the electrodes is formed by an edge of a prism, said edge being placed parallel to a propagation axis of the light emitted by the light source.

11. The smoke detector according to claim 1, wherein the concentration means comprise a focusing means configured to focus light rays in the detection area, to generate electromagnetic field gradients in the detection area.

12. The smoke detector according to claim 1, wherein the light source is configured to emit a beam of light rays with a wavelength between 800 nm and 1000 nm.

13. The smoke detector according to claim 1, further comprising means of powering the light source configured to supply current pulses to the light source with amplitude AI and duration ΔTi between 100 ns and 1 ms.

14. The smoke detector according to claim 13, wherein voltage pulses are applied with a delay ΔT1 after the current pulses are emitted, the delay ΔT1 being between 0 and 60 µs.

15. The smoke detector according to claim 1, further comprising means of processing the electric reception signal configured to analyze the temporal variation in the amplitude of the electric reception signal.

16. The smoke detector according to claim 14, wherein the processing means are configured to compare the amplitude of the signal to a reference level determined by reference means, the reference means being configured to modify the reference level according to values of a previously measured electric signal and/or according to the nature of the fire risk to be monitored.

17. The smoke detector according to claim 1, wherein the non-uniform electromagnetic field is configured to aggregate the smoke particles in the concentration area to form larger smoke particles.

18. The smoke detector according to claim 1, wherein:
   the light receiver is configured to receive, in the presence of smoke particles or aggregates of smoke particles in the detection area, diffused light coming from the detection area, and
   the chamber is configured to minimize the penetration of exterior light into the detection area and the source and the receiver being placed relative to each other to configured to prevent the light emitted by the source reaching the receiver directly.

19. A method for detecting smoke, comprising:
   emitting a beam of light rays P from a light source towards a detection area in a chamber provided with apertures configured to allow the smoke to enter a detection area;
   receiving, with a receiver, in the presence of smoke particles or aggregates of smoke particles in the detection area, of light coming from the detection area; and providing an electric reception signal representative of the received light; and
   generating a non-uniform electromagnetic field in at least one portion of the detection area, so that, in the presence of smoke, smoke particles entering the sub-area of the detection area are polarized by the electromagnetic field, the electromagnetic field applying a dielectrophoretic force on the smoke particles in order to drive the polarized smoke particles into a concentration area in the detection area.

20. The method according to claim 19, further comprising aggregating smoke particles to each other in the concentration area to form larger smoke particles.

* * * * *